(12) United States Patent
Hall

(10) Patent No.: US 6,520,926 B2
(45) Date of Patent: *Feb. 18, 2003

(54) COMPRESSION SUPPORT SLEEVE

(75) Inventor: Michael R. Hall, Topeka, KS (US)

(73) Assignee: Lohmann Rauscher, Inc., Topeka, KS (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/256,755

(22) Filed: Feb. 24, 1999

(65) Prior Publication Data

US 2002/0082542 A1 Jun. 27, 2002

(51) Int. Cl.$^7$ .......................... A61F 13/00; A61F 15/00
(52) U.S. Cl. ........................................... 602/64; 602/75
(58) Field of Search ................. 602/60–64, 52, 602/54, 55, 75–77, 900, 903, 904, 5; 442/149–150

(56) References Cited

U.S. PATENT DOCUMENTS

| 2,238,878 A | | 4/1941 | Baitz et al. | |
| 2,310,082 A | * | 2/1943 | Holbrooke | 602/75 X |
| 2,592,801 A | * | 4/1952 | Hanington | 602/75 |
| 2,787,266 A | | 4/1957 | Scholl | |
| 2,811,154 A | | 10/1957 | Scholl | |
| 3,457,919 A | | 7/1969 | Harbard | |
| 3,880,155 A | * | 4/1975 | Rosoff | 602/8 |
| 3,983,870 A | | 10/1976 | Herbert et al. | |
| 4,445,505 A | * | 5/1984 | Labour et al. | 602/26 |
| 4,699,133 A | | 10/1987 | Schafer et al. | |
| 4,832,010 A | * | 5/1989 | Lerman | 602/63 |
| 4,838,253 A | | 6/1989 | Brassington et al. | |
| 4,944,958 A | | 7/1990 | Langen et al. | |
| 5,085,210 A | * | 2/1992 | Smith, III | 602/26 |
| 5,156,589 A | | 10/1992 | Langen et al. | |
| 5,277,954 A | * | 1/1994 | Carpenter | 428/71 |
| 5,413,553 A | * | 5/1995 | Downes | 602/64 X |
| 5,418,980 A | * | 5/1995 | Kelly | 2/170 |
| 5,449,341 A | * | 9/1995 | Harris | 602/63 |
| 5,497,513 A | * | 3/1996 | Arabeyre et al. | 2/16 X |
| 5,607,749 A | * | 3/1997 | Strumor | 428/156 |
| 5,635,201 A | | 6/1997 | Fabo | |
| 5,735,807 A | | 4/1998 | Cropper | |
| 5,865,776 A | * | 2/1999 | Springs | 602/26 |
| 5,916,187 A | * | 6/1999 | Brill | 602/75 X |
| 5,948,707 A | * | 9/1999 | Crawley et al. | 442/101 |

* cited by examiner

Primary Examiner—Denise M. Pothier
(74) Attorney, Agent, or Firm—John C. McMahon

(57) ABSTRACT

A multilayer compression support sleeve construction. The laminate material includes a thin polyurethane film coated on both surfaces with an adhesive. A stretchable elastomeric polymer material is bonded to each of the adhesive surfaces. A substantial portion of one of the elastomeric polymer surfaces is coated with a discontinuous layer of silicone microdots. The microdots are applied by gravure roll printing to project a uniform distance above the elastomeric polymer surface to form small tacky dots. The laminate material is fabricated into a sleeve with the material oriented so that the microdot coated face is adjacent the skin of the wearer. Microdots may be applied in a predetermined pattern in order to impart enhanced compression to certain areas of the support sleeve. The resulting support sleeve retains its breathability while presenting a nonslip inner surface which prevents migration of the garment on the skin of the wearer during exercise. The garment does not cause irritation to the underlying skin.

9 Claims, 2 Drawing Sheets

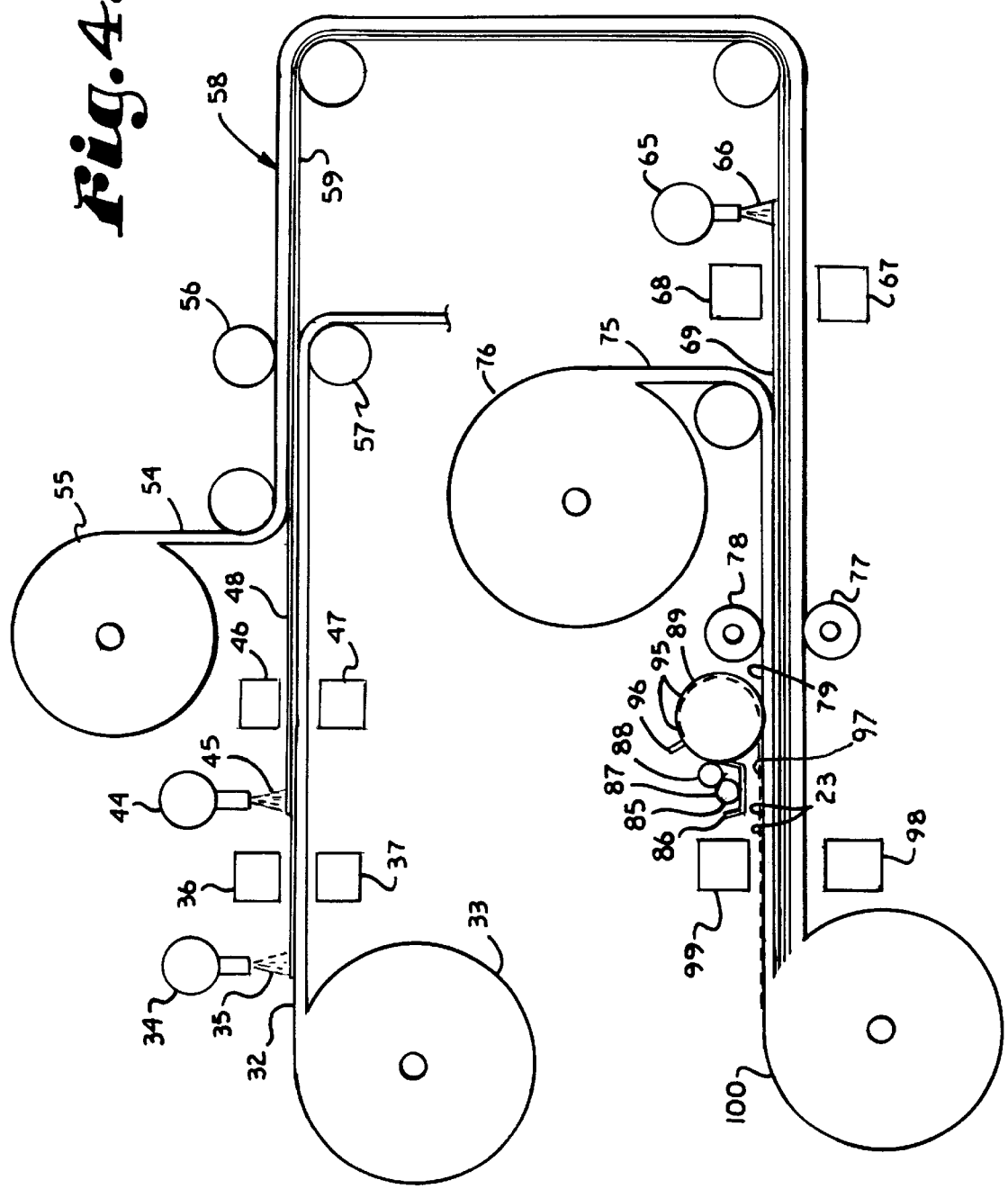

COMPRESSION SUPPORT SLEEVE

BACKGROUND OF THE INVENTION

The present invention is directed to an improved compression support sleeve constructed to stay comfortably in place during strenuous activity without the need for stays or straps and without causing irritation of the underlying skin. More particularly, it is concerned with a sleeve of laminate multilayer construction having a skin-contacting surface substantially coated with a thin layer of discontinuous silicone microdots. Advantageously, the resulting sleeve construction is freely stretchable to conform to the muscles and joints of a user, while providing slip-resistant support and augmented compression without impairing breathability of the device.

The upright posture of the human body renders it particularly susceptible to strains, sprains and other injuries which are generally manifested by swelling, inflammation and discomfort. When severe, an injury may result in impaired mobility and necessitate restriction of movement and activity. The body is also subject to formation of fibrin clots which may obstruct vessels in the peripheral circulation when the body is in the prone position for prolonged periods. In addition to localized morbidity, such clots may also break free and travel to the heart or lungs causing more serious damage.

Orthopedic injuries have economic as well as physical repercussions for professional athletes engaged in competitive sports. Sidelined athletes lose not only the opportunity to perform, but experience a reduction in their overall level of fitness during periods of restricted activity, necessitating a period of retraining prior to resumption of competition. Of course, most individuals are not professional athletes and they engage in less strenuous activities such as jogging, calisthenics, walking and occasional competitive sports.

However, non professional athletes also experience discomfort when injured and their level of physical fitness is also impaired by injury-enforced inactivity. Moreover, amateur athletes may be more likely to be susceptible to injury, since they generally lack the advice of professional trainers as well as the fitness and judgment developed by professional athletes. Those who engage in infrequent bouts of strenuous exercise without training are most at risk of injury. However, even the well-trained amateur athlete is subject to occasional strains and sprains. Some individuals are particularly at risk of injury because of previous traumatic injury which has left continuing weakness in a joint or limb. Other individuals are at greater risk because of their advanced age or general state of health and fitness.

The importance of providing compression support to limbs and joints which have been injured or weakened or which are subject to stress, such as may be caused by strenuous exercise, is well recognized. So-called R.I.C.E. therapy (rest, ice, compression, elevation) is commonly recommended for implementation following minor athletic injuries. Such therapy is known to be particularly effective when cold and compression are applied immediately following an injury and the compression is continued for a period of about 24 to 48 hours. The need to provide compression to facilitate venous return in bed bound patients in order to prevent formation of blood clots is similarly well recognized.

Orthopedic compression bandages, braces and sleeves have long been employed to provide support for athletic and medical purposes. They are commonly worn over the wrists, elbows, knees and ankles. They are also frequently employed on the lower legs and forearms, and, less frequently, on the upper legs and arms, shoulders and chest. They provide support during normal movement, which support may be especially required by persons recovering from previous injuries or by persons who are frail or elderly. Such compression devices also provide support for ligaments, tendons, muscles and joints against the stresses of over extension which may occur during exercise. In this manner, they help to prevent orthopedic and muscular injury or reinjury. Elastomeric sleeves have also been employed, commonly in the form of stockings, to provide compression in order to facilitate peripheral venous return from the legs of bed bound patients, thereby helping to prevent embolism.

Such compression support devices are often of elastomeric construction, either in the form of sleeves, dressings or strips which may be slipped over or wound around the affected area and fastened by means of hook and loop fasteners or specialized clips or pins.

A number of materials have been employed in the construction of such support devices. Dressing, strip and sleeve-type supports are generally constructed of knitted or woven elastic webbing consisting of elastic or cotton-wound elastic threads or of stretchable synthetic resin compositions such as neoprene. Laminate multilayer composite materials have recently become available which are thinner than previously used woven elastics and especially neoprene. Such multilayer materials may be fabricated into sleeve or bandage-type supports. They are often five layers thick, with a synthetic resinous film layer sandwiched between two adhesive layers, each of which is covered by an outer layer of a stretchable synthetic fabric such as nylon. However, the skin-contacting layer is quite slick, and the support tends to migrate along the skin unless it is sized and custom fitted to the limb of a wearer. This is especially true of supports placed about the knee as such supports slip or migrate along the leg.

Known knitted, woven and laminate materials tend to experience slippage along the limb and to wrinkle or bunch up, causing compression of the limb to be uneven. Such shifting and uneven displacement of the material against the skin causes dermal irritation and discomfort to the wearer. Slippage of laminate supports can be limited, but not eliminated by custom fitting. However, such fitting requires personal consultation with a professional fitter. Thus, it is expensive and consequently unavailable to most users. Moreover, changes in body weight, weight distribution or development of musculature because of growth, exercise or aging may necessitate periodic refitting of the brace to maintain proper support.

Because of these problems, some braces have been constructed of rubber-like polymeric materials such as neoprene, which tends to stay in place because of its high coefficient of friction against the skin. Neoprene supports are generally thicker and bulkier than braces constructed of other materials, and such materials have not proven to be satisfactory for frequent or sustained use because of their lack of permeability to air and water. Supports constructed of neoprene do not permit the underlying skin of the wearer to breathe. Because such impermeable supports lack ventilation to carry away body heat and moisture, extended or frequent wear may be uncomfortable as well as irritating to the skin. If such irritation is prolonged, it can result in morbidity such as dermatitis and sloughing of the skin. Such impermeable materials are especially unsuitable for compression bandages to be worn by amputees or individuals with impaired circulation, who may develop necroses. In addition, since impermeable supports provide no outlet for perspiration excreted by the wearer, a salt residue is deposited on the inner surface of the support which eventually serves to impair elasticity and shorten its effective life span.

Since braces constructed entirely of impermeable, slip-resistant materials have not proven to be satisfactory, attempts have been made to construct braces from a combination of elastomeric and slip-resistant materials. One current technique is to apply a continuous bead or band of a slip-resistant material such as silicone around the upper inner surface of the support. Certain applications, such as ankle braces, may require bands at both the upper and lower inner surfaces in order to control slippage. However, the slip-resistant material is impermeable, lacks ventilation, and is consequently uncomfortable against the skin of the wearer. Such bands project inwardly against the skin, causing additional compression and discomfort. In addition, because the band is of necessity localized at the top of the support and is fairly narrow, it is not entirely effective in preventing slippage.

None of the previously available materials and combinations of materials provide effective elastomeric support and compression while staying in place and maintaining breathability for the underlying skin surface. Accordingly, there is a need for a compression support sleeve for athletic and medical uses which is light weight, comfortable, stretchable to conform to the anatomy of a user and to permit movement, which resists shifting against the skin and migration during exercise and which does not impair breathability of the underlying skin or circulation of the underlying blood vessels.

SUMMARY OF THE INVENTION

The present invention resolves the problems previously outlined and provides a greatly improved compression support sleeve which is comfortable, freely stretchable and breathable and is especially designed to stay in place and to minimize skin irritation.

The support sleeve includes a multilayer laminate material formed into a tube or other compression structure which is constructed to conform in shape to an intended limb or joint. The sleeve may be tailored with gussets or darts to improve the fit, and may be equipped with one or more support stays or pulls to facilitate placing the sleeve on the user. The laminate material includes a polyurethane film having an adhesive coating applied to either side. The adhesive coatings are each bonded to respective layers of a stretchable elastomeric polymer material. The inner elastomeric polymer surface of the sleeve, which faces the skin of the wearer, is substantially coated with a discontinuous layer of silicone microdots. The microdot-imprinted surface remains permanently tacky, serving to prevent slippage of the finished support garment while the spacing between the microdots facilitates "breathing" of the material.

In particularly preferred forms, the silicone is applied by gravure roll printing during manufacture of the sleeve to provide microdots having a uniform depth. The support may be worn repeatedly and laundered without loss of friction by the silicone-coated surface.

OBJECTS AND ADVANTAGES OF THE INVENTION

The principal objects and advantages of the present invention are: to provide a compression support which stays in place on the body of a wearer while maintaining breathability of the underlying skin; to provide such a support which is of multilayer laminate construction; to provide such a support which is light weight and comfortable to a wearer; to provide such a support which does not irritate the skin of a wearer; to provide such a support which has enhanced compression properties; to provide such a support which eliminates the requirement of rigid or semi-rigid shape maintaining structure such as stays, straps or sewn in elastic or impermeable compositions to prevent garment migration; to provide a material for such a support which has a skin-contacting surface having a high coefficient of friction as well as allowing breathability; to provide such a material which reduces garment migration; to provide such a which reduces the likelihood of skin irritation caused by shifting of the material against the skin; to provide such a material which imparts additional compression to a garment; to provide such a material which is coated with a matrix of tacky microdots; to provide such a material which is coated with a matrix of silicone microdots; to provide such a material which is coated with a matrix of tacky microdots in an identifying pattern; to provide such a material which is comfortable to wear; to provide such a material upon which the microdots are gravure printed with silicone; and to provide a method for making a material for such a support which is simple and efficient and economical to manufacture, which effectively provides a non slip yet breathable elastomeric surface, and which is particularly well-adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 4 is a schematic diagram illustrating a method of making a multilayer laminate material for use in construction of the support device.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and-functional details disclosed herein are not to be interpreted as limiting, but merely as a basis for the claims and as a representative basis for teaching one skilled in the art to variously employ the present invention in virtually any appropriately detailed structure.

Figure 1:
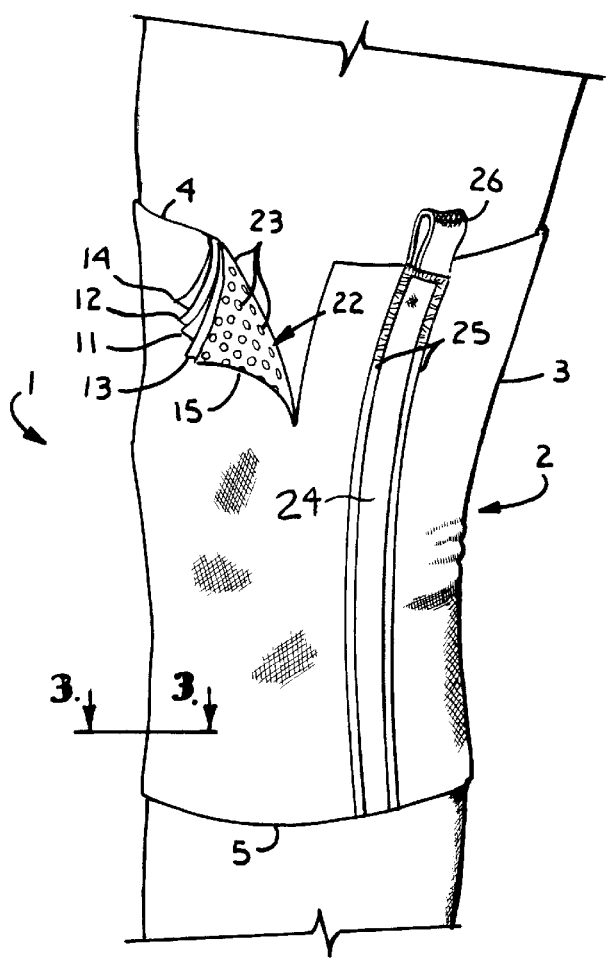
FIG. 1 is a side elevational view of a support device in accordance with the present invention shown placed on the leg of a user, with a portion of the support laid back so as to illustrate the multilayer laminate construction thereof.
Figure 2:
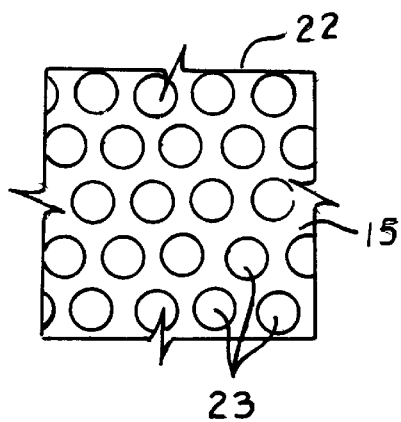
FIG. 2 is a fragmentary side view of an inner surface of the support device.
Figure 3:
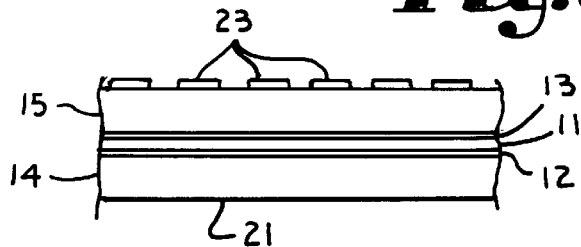
FIG. 3 is a fragmentary cross-sectional view of the support device, taken along line 3—3 of FIG. 1.

The reference numeral 1 generally identifies a compression support sleeve in accordance with the present invention and the sleeve 1 is depicted in place over human leg knee joint area 2. The sleeve 1 includes a generally tube-shaped member 3 of multilayer construction, having an upper end 4 and a lower end 5. As best shown in FIGS. 1 and 3, a central film 11 is sandwiched between outer and inner adhesive layers 12 and 13. A flexible and resilient film composition is required for the film 11 in order to permit stretching of the sleeve 1, as it is put on and to accommodate movement of the underlying joint or limb during use. Polyurethane having a thickness of about 2 mil is preferred, although another suitable polymeric film may be employed and thickness may vary in accordance with desired characteristics of the sleeve 1. The adhesive or heat and pressure sensitive glue layers are bonded respectively to outer and inner layers of elastomeric polymer material 14 and 15. Any suitable adhesive which is compatible with both the polyurethane film layer 11 and the elastomeric polymer layers 14 and 15 may be employed. The polymer layers 14 and 15 are preferably constructed of a spandex fiber such as is sold under the trademark Lycra by DuPont Chemical Co., however, other materials function satisfactorily for the purpose.

The outer elastomeric polymer layer 14 presents a smooth surface 21, which facilitates free movement of clothing over the sleeve 1, while providing resistance to abrasion and wear. Various constructions of sleeves having layers similar to layers 11, 12, 13, 14 and 15 have been previously offered by others for such devices as wet suits and medical devices. Such a sleeve of five layers is depicted in U.S. Pat. No. 5,735,807 of Cropper for use as a knee compression support, which is incorporated herein by reference.

An inner, slip resistant surface 22 is formed by a layer of discontinuous microdots of a tacky substance 23, which covers a substantial portion of the surface 21. Silicone has been found to be particularly suitable for this purpose because it is extremely compatible with human skin, and may be compounded into an adhesive fluid for application which retains a slightly tacky surface when dry.

The microdots 23 are spaced and preferably of generally circular configuration, having a thickness of from about 1 to 4 mils, preferably about 2 mils, and with a diameter of from about 10 to 50 mils in diameter with about 25 mils in diameter being preferred. Also, preferably the dots are spaced a distance from each other approximately equal to the radius of the dots. Also, preferably the dots are spaced a distance from each other approximately equal to the radius of the dots. The microdots 23 are imprinted upon the fabric by application of a preselected pressure which causes them to extend outwardly from the fabric surface 22 preferably about 2 mils. The microdots 23 are applied over substantially all of the inner surface 22 of the polymer layer 15. Because of the elastomeric nature of silicone patterns when stretched, the silicone microdots 23 impart additional compression to the garment 1 and spacing facilitates breathing of the fabric. In certain embodiments, the size and distribution of the microdots 23 are varied in order to provide additional compression at predetermined locations. Such variable compression enables the garment to provide differential support and is particularly desirable in certain applications such as, for example, ankle braces.

While the microdots can be constructed of any material compatible with the skin a silicon rubber is preferable, especially a silicon rubber that is the reaction product of 5 to 10% VI/ST dimethyl-methylvinylsiloxane, 60 to 80% vinylpolydimethylsiloxane, 10 to 30% D4 and HMDZ treated silicon dioxide reacted with 60 to 80% vinylpolydimethylsiloxane, 5 to 10% VI/ST dimethylvinylsiloxane, 1 to 5% polymethylhydrogensiloxane and 10 to 30% D4 and HMDZ treated silicon dioxide. Such a composition is available from Enterprise Coatings Co. Ltd.

While normally not necessary with the microdots 23, the sleeve 1 may also include one or more ribs or stays 24, which are formed of a flexible synthetic resinous material to impart additional rigidity and support to the garment or assist in application of the sleeve 1 to the knee joint 2. The stays 24 are secured in place on either side and at the ends by seams 25, which may be sewn or fusion welded. One or more loops 26 extend upwardly from sleeve upper end 4 to facilitate pulling the garment on and positioning it snugly in place over a selected limb or joint.

While a generally tubular sleeve 1 has been depicted and described, those skilled in the art will appreciate that such compression support garments may be fabricated to include gussets or seams or in the form of stockings, spiral constructions for use on the ankles and elbows as well as planar bandages which may be wound around a limb or joint in overlapping fashion and held in place by hook and loop fasteners or clips.

A method of manufacture of the material of sleeve 1 is depicted schematically in FIG. 4 which includes providing a substrate 32 having suitable release properties to permit casting and easy removal of a polyurethane solution. The substrate 32 is preferably supplied on a spool 33. As the substrate 32 is unrolled into an assembly line, it passes a spray station 34, which applies a polyurethane fluid 35 to one surface of the substrate 32. The polyurethane coated substrate 32 passes through a series of drying ovens 36 and 37, which dry the polyurethane 35 into a 2 mil film 59 on the substrate 32.

The film-coated substrate passes a spray station 44, which applies an adhesive solution 45 onto the surface. Preferably, the station 44 sprays adhesive solution 45 onto the film-coated substrate in an even, continuous layer. In other alternate embodiments, the spray station 44 may be operated intermittently or the distance between the spray heads may be set to deliver a discontinuous layer of adhesive solution 45. Once coated with adhesive solution 45, the polyurethane film-coated substrate 32 passes through a second series of ovens 46 and 47, where the solvent is evaporated from the adhesive solution to form an adhesive layer 48.

Elastomeric fabric 54, such as a spandex fiber of about 20 mils, is supplied, preferably on a spool 55. Knitted nylon tricot fabric, especially as sold under the trademark LYCRA by E. I. DuPont de Nemours, is preferred because it provides a superior laminate construction which is long wearing and extremely comfortable to the wearer, although any other suitable knitted, woven or nonwoven fabric such as cotton, rayon, other stretchable synthetic fiber or blend thereof may be employed. The fabric 54 is unwound onto the surface of the adhesive layer 48 and is pressed into the adhesive 48 at elevated temperature by a series of rollers 56 and 57 to form a fabric/adhesive/film laminate 58. The laminate 58 is then stripped from the substrate 32, exposing an uncoated polyurethane film surface 59.

The laminate 58 passes a spray station 65 which again sprays an adhesive solution 66 onto the uncoated polyurethane film surface 59. Once coated with adhesive solution 66, the laminate 58 passes through a third series of drying ovens 67 and 68, where the solvent is evaporated from the adhesive solution to form an adhesive layer 69.

Additional elastomeric tricot fabric 75 of about 20 mils in thickness is supplied on a spool 76. The fabric 75 is unwound onto the surface of the adhesive layer 69 and is pressed into the adhesive 69 by rollers 77 and 78 to form a fabric/adhesive/polyurethane/adhesive/fabric laminate material 79.

The silicone microdots 23 are applied to one of the fabric surfaces of the laminate 79 by a process such as gravure printing. In the preferred rotogravure method, a suitably compounded silicone fluid 85 is supplied in a trough 86 for imprinting onto one surface of the laminate. Silicone is preferred because of the compatibility of its cured silicone gel with the skin and because the cured gel retains a slightly tacky surface having a high coefficient of friction against the skin.

A first rotating cylinder 87 rests in the trough 86, and by rotary movement thereof, its surface receives a coating of the silicone 85. A second rotating cylinder 88, is positioned in contact with cylinder 87 and elevated slightly above the trough 86 so as to receive a coating of the silicone solution 85 from the first cylinder 87 during rotation, and to permit any excess solution to drain back into the trough 86. A rotating gravure cylinder 89 is positioned so as to make contact with cylinder 88 as well as the surface of laminate 79 during its rotation.

The surface of cylinder 89 is etched or engraved to form a preselected pattern of spaced, generally circular recesses 95, each having a predetermined diameter and depth. As gravure cylinder 89 rotates against cylinder 88, the recesses 95 are filled with silicone 85. A doctor blade 96 removes the excess silicone 85 from the surface of the gravure cylinder 89, but not from the recesses. Continued rotation of the gravure cylinder 89 brings the silicone filled recesses 95 into contact with the surface of laminate 79, where the silicone 85 is imprinted as raised silicone microdots 23.

Gravure cylinder 89 exerts a preselected pressure against the laminate 79 during the printing process in order to achieve a selected depth of imprint of the microdots 23 into the laminate 79. In this manner, the depth of the recesses 95 and imprinting pressure cooperatively determine the depth of the imprinted microdots 23 on the surface of the imprinted laminate 97 The size, depth, distribution and arrangement of the recesses 95 on the gravure cylinder 89 may be preselected to imprint microdots 23 in any desirable pattern which serves to reduce garment migration, provide additional areas of compression, or even to provide brand identification.

The imprinted laminate 97 passes through a series of circulating air ovens 98, 99 for evaporation of any solvent residue and curing of the silicone solution to a tacky gel. The laminate 97 is then wound onto rolls 100 of manageable size. The silicone imprinted laminate 97 may also be joined under heat and pressure with a release-coated protective backing prior to winding on rolls 100. The backing may be removed after complete cure of the silicone, to expose a multilayer laminate material having a permanently tacky imprinted surface with spacing between the dots to facilitate breathing of the material.

The material thus produced may be formed into completed sleeves 1, stockings and other types of compression support having sewn or fused darts, gussets, and seams. The supports may also include fasteners such as for example, hooks, zippers, buttons and the like.

It is to be understood that while certain forms of the present invention have been illustrated and described herein, it is not to be limited to the specific forms or arrangement of parts described and shown.

What is claimed and desired to be secured by Letters Patent is as follows:

1. A stretchable and breathable laminate compression knee support comprising an elongate and comparatively thin sleeve sized and shaped to extend partly along the leg on either side of a user's knee; said sleeve including:

a) a first interior layer of an elastomeric fiber material;

b) a second layer of a polymeric film, said film presenting a pair of opposed surfaces;

c) an exterior third layer of an elastomeric fiber material;

d) a pair of adhesive fourth and fifth layers bonding said first and third layers to respective second layer opposed surfaces; each of said first, second, third, fourth and fifth layers being breathable and being joined together to form a sleeve of continuous laminate sized, shaped and constructed to snugly and elastically encircle a knee region of a user;

e) said first layer of elastomeric fiber having an inner surface that is adopted to engage the knee region; said inner surface being substantially imprinted with a pattern of spaced silicon dots and having spacing between said dots so as to allow breathing through the layers of the support; said dots having a low profile with a thickness between about 1 to 4 mils and being tacky with respect to skin so as to be adapted to resist slippage and bunching of said support device over said entire inner surface during use; said pattern of dots being distributed relatively evenly on said inner surface so as to alternate with breathable portions of said inner surface generally over said entire inner surface, so as to allow breathing throughout said entire inner surface; and f) the inner surface being uncoated in said spacing breathable material except for said dots to enhance breathing from said knee region through said support and so as to permit dissipation of heat and moisture from an underlying skin surface during use through the uncoated inner surface.

2. The support according to claim 1 wherein said elastomeric fiber material is a spandex fiber.

3. The support according to claim 1 wherein said polymeric film is polyurethane.

4. The support according to claim 1 wherein said sleeve is cylindrical in shape and continuous.

5. A stretchable and breathable laminate compression knee support comprising an elongate and comparatively thin sleeve sized and shaped to extend partly along the leg on either side of a user's knee; said sleeve including:

a) a first interior layer of an elastomeric fiber material;

b) a second layer of a polymeric film, said film presenting a pair of opposed surfaces;

c) an exterior third layer of an elastomeric fiber material;

d) a pair of adhesive fourth and fifth layers bonding said first and third layers to respective second layer opposed surfaces; each of said first, second, third, fourth and fifth layers being breathable and being joined together to form a sleeve of continuous laminate sized, shaped and constructed to snugly and elastically encircle a knee region of a user;

e) said first layer of elastomeric fiber having an inner surface that is adopted to engage the knee region; said inner surface being substantially imprinted with a pattern of spaced silicon dots with each dot having a maximum width and having spacing between said dots so as to allow breathing through the layers of the support; said dots having a low profile with a thickness between about 1 to 4 mils and being tacky with respect to skin so as to be adapted to resist slippage and bunching of said support device over said entire inner surface during use; said dots each being spaced from adjacent dots less than the width of said dots; said pattern of dots being distributed relatively evenly on said inner surface so as to alternate with breathable portions of said inner surface generally over said entire inner surface, so as to allow breathing throughout said entire inner surface; and f) the inner surface being uncoated in said spacing to enhance breathing from said knee region through said support and so as to permit dissipation of heat and moisture from an underlying skin surface during use through the uncoated inner surface.

6. A stretchable and breathable laminate compression knee support comprising an elongate and comparatively thin sleeve sized and shaped to extend partly along the leg on either side of a user's knee; said sleeve including;

a) a first interior layer of an elastomeric fiber material;

b) a second layer of a polymeric film, said film presenting a pair of opposed surfaces;

c) an exterior third layer of an elastomeric fiber material;

d) a pair of adhesive fourth and fifth layers bonding said first and third layers to respective second layer opposed surfaces; each of said first, second, third, fourth and fifth layers being breathable and being joined together to form a sleeve of continuous laminate sized, shaped and constructed to snugly and elastically encircle a knee region of a user;

e) said first layer of elastomeric fiber having an inner surface that is adopted to engage the knee region; said inner surface being substantially imprinted with a pattern of spaced silicon dots and having spacing between said dots so as to allow breathing through the layers of the support; said dots having a low profile with a thickness between about 1 to 4 mils and being tacky with respect to skin so as to be adapted to resist slippage and bunching of said support device over said entire inner surface during use; said pattern of dots being distributed relatively evenly on said inner surface so as to alternate with breathable portions of said inner surface generally over said entire inner surface, so as to allow breathing throughout said entire inner surface; the size and distribution of said dots in said pattern being varied in order to provide the support with selected areas of variable compression; and f) the inner surface being uncoated in said spacing to enhance breathing from said knee region through said support and so as to permit dissipation of heat and moisture from an underlying skin surface during use through the uncoated inner surface.

7. A stretchable and breathable laminate compression knee support comprising an elongate and comparatively thin sleeve sized and shaped to extend partly along the leg on either side of a user's knee; said sleeve including;

a) a first interior layer of an elastomeric fiber material;

b) a second layer of a polymeric film, said film presenting a pair of opposed surfaces;

c) an exterior third layer of an elastomeric fiber material;

d) a pair of adhesive fourth and fifth layers bonding said first and third layers to respective second layer opposed surfaces; each of said first, second, third, fourth and fifth layers being breathable and being joined together to form a sleeve of continuous laminate sized, shaped and constructed to snugly and elastically encircle a knee region of a user;

e) said first layer of elastomeric fiber having an inner surface that is adopted to engage the knee region; said inner surface being substantially imprinted with a pattern of spaced silicon dots and having spacing between said dots so as to allow breathing through the layers of the support; said dots having a low profile with a thickness between about 1 to 4 mils and being tacky with respect to skin so as to be adapted to resist slippage and bunching of said support device over said entire inner surface during use; said dots having a maximum diameter of 50 mils; said pattern of dots being distributed relatively evenly on said inner surface so as to alternate with breathable portions of said inner surface generally over said entire inner surface, so as to allow breathing throughout said entire inner surface; and f) the inner surface being uncoated in said spacing to enhance breathing from said knee region through said support and so as to permit dissipation of heat and moisture from an underlying skin surface during use through the uncoated inner surface.

8. The support according to claim 7 wherein:

a) said dots have a diameter that is within the range of from about 10 mils to 50 mils.

9. The support according to claim 7 wherein;

b) said dots have a diameter of about 25 mils.

* * * * *